(12) United States Patent
Tsinberg et al.

(10) Patent No.: US 9,040,255 B2
(45) Date of Patent: May 26, 2015

(54) USE OF DIAZOLIDINYL UREA FOR ANTI-CLUMPING OF BIOLOGICAL SAMPLES

(75) Inventors: Pavel Tsinberg, San Diego, CA (US); Stephen D. Mikolajczyk, San Diego, CA (US)

(73) Assignee: BIOCEPT, INC., San Diego, CA (US)

( * ) Notice: Subject to any disclaimer, the term of this patent is extended or adjusted under 35 U.S.C. 154(b) by 0 days.

(21) Appl. No.: 13/243,432

(22) Filed: Sep. 23, 2011

(65) Prior Publication Data

US 2012/0164676 A1    Jun. 28, 2012

Related U.S. Application Data

(60) Provisional application No. 61/385,935, filed on Sep. 23, 2010.

(51) Int. Cl.
| | |
|---|---|
| B01L 3/00 | (2006.01) |
| G01N 1/28 | (2006.01) |
| C12Q 1/02 | (2006.01) |
| A61B 10/02 | (2006.01) |
| A61B 5/15 | (2006.01) |
| A61B 5/154 | (2006.01) |
| G01N 33/543 | (2006.01) |

(52) U.S. Cl.
CPC .............. *A61B 10/02* (2013.01); *A61B 5/1405* (2013.01); *A61B 5/150343* (2013.01); *A61B 5/150755* (2013.01); *A61B 5/154* (2013.01); *G01N 33/54393* (2013.01)

(58) Field of Classification Search
None
See application file for complete search history.

(56) References Cited

U.S. PATENT DOCUMENTS

| | | |
|---|---|---|
| 5,196,182 A | 3/1993 | Ryan |
| 5,250,438 A | 10/1993 | Ryan |
| 5,260,048 A | 11/1993 | Ryan |
| 5,459,073 A | 10/1995 | Ryan |
| 5,460,797 A | 10/1995 | Ryan |
| 5,811,099 A | 9/1998 | Ryan |
| 5,849,517 A | 12/1998 | Ryan |
| 6,200,500 B1 | 3/2001 | Ryan |
| 6,221,668 B1 | 4/2001 | Ryan |
| 6,337,189 B1 | 1/2002 | Ryan |
| 6,399,388 B1 | 6/2002 | Ryan |
| 6,403,377 B1 | 6/2002 | Ryan |
| 6,406,915 B2 | 6/2002 | Ryan |
| 6,653,137 B2 | 11/2003 | Ryan |
| 6,723,563 B2 | 4/2004 | Ryan |
| 6,794,152 B2 | 9/2004 | Ryan |
| 6,977,156 B2 | 12/2005 | Ryan |
| 7,247,484 B2 | 7/2007 | Ryan |
| 7,361,513 B2 | 4/2008 | Ryan |
| 7,419,832 B2 | 9/2008 | Hunsley |
| 7,608,457 B2 | 10/2009 | Hunsley |
| 7,618,821 B2 | 11/2009 | Ryan |
| 7,767,460 B2 | 8/2010 | Hunsley |
| 2002/0086346 A1 | 7/2002 | Ryan |
| 2004/0137417 A1* | 7/2004 | Ryan ............................. 435/2 |
| 2006/0047221 A1 | 3/2006 | Gu |
| 2009/0081678 A1 | 3/2009 | Ryan |
| 2010/0047905 A1 | 2/2010 | Ryan |
| 2010/0086962 A1 | 4/2010 | Hunsley |
| 2010/0167271 A1 | 7/2010 | Ryan |
| 2010/0184069 A1 | 7/2010 | Fernando |
| 2010/0209930 A1 | 8/2010 | Fernando |
| 2010/0317107 A1 | 12/2010 | Ryan |

OTHER PUBLICATIONS

ISR for PCT/US2011/053041 mailed Apr. 26, 2012.
IPRP for PCT/US2011/053041 issued Mar. 26, 2013; Written Opinion for PCT/US2011/053041 completed Apr. 26, 2012.

* cited by examiner

*Primary Examiner* — Blaine Lankford
*Assistant Examiner* — David Berke-Schlessel
(74) *Attorney, Agent, or Firm* — Cooley LLP

(57) ABSTRACT

The present invention provides methods for preventing clumping of cells in microfluidic devices by addition of diazolidinyl urea (DU). DU can be added to samples at the time of collection or can be added to samples post-collection. DU can also be pre-added to sample collection devices.

11 Claims, 4 Drawing Sheets

USE OF DIAZOLIDINYL UREA FOR ANTI-CLUMPING OF BIOLOGICAL SAMPLES

RELATED APPLICATIONS

This application claims priority to U.S. Provisional Application No. 61/385,935 filed Sep. 23, 2010, which is hereby incorporated by reference in its entirety.

FIELD OF THE INVENTION

This invention relates to the use of diazolidinyl urea (DU) and its related compounds, e.g., the use of DU to prevent cell clumping in biological samples.

BACKGROUND OF THE INVENTION

When biological samples including cells or cellular components are collected and/or processed for testing, these cells or cellular components can clump or stick together. This could be problematic for the testing down stream, e.g., this may block the flow of fluid through testing devices or make sample analysis difficult. In particular, whenever samples are "stressed" either through shipment or pre-processing, they begin to clump up when passing through testing devices, e.g., microfluidic devices. For example, older samples and samples from patients with medical conditions accentuate such clumping effect even further. In addition, pre-processing of samples, for example, through density gradients or centrifugation steps activates the clumping effect.

There is a need in the field for methods or reagents useful for addressing the cell clumping issue in sample collection and processing.

BRIEF SUMMARY OF THE INVENTION

The present invention is based at least in part on the discovery that diazolidinyl urea or its derivatives or analogs can be used to prevent or reduce cell clumping in biological samples. Accordingly the present invention provides methods and devices useful for preventing or reducing cell clumping in biological samples. In some embodiments, the present invention provides methods for inhibiting cellular clumping in a biological sample by mixing an effective amount of diazolidinyl urea (DU) with the sample, e.g., where the cellular clumping is reduced at least 50% in the presence of DU compared to the absence of DU in the sample.

In some embodiments, the effective amount of diazolidinyl urea is at least 0.01%-3%.

In some embodiments, the method includes mixing an effective amount of diazolidinyl urea in a combination with a non-chelating agent based anti-coagulating agent with the biological sample. In some embodiments, the methods include mixing an effective amount of diazolidinyl urea in combination with acid citrate dextrose (ACD) with the biological sample.

In some embodiments, the diazolidinyl urea is mixed with the biological sample before or during biological sample testing.

In some embodiments, the diazolidinyl urea can be in a solid or liquid form in a container, where the biological sample is added to the container.

In some embodiments, the biological sample is selected from the group consisting of whole blood, blood serum, plasma and bone marrow.

The present invention also provides a container for collecting biological samples comprising an effective amount of diazolidinyl urea in combination with a non-chelating agent based anti-coagulating agent. In some embodiments, the volume of the container is from about 0.5 mL to about 50 mL and the diazolidinyl urea is in an amount from about 0.02 grams to about 30 grams. In some embodiments, the non-chelating agent based anti-coagulating agent in the container is acid citrate dextrose. In some embodiments, the container comprises a biological sample. In some embodiments, the diazolidinyl urea in the container is in a liquid or solid form.

The present invention also provides a container for collecting biological samples comprising an effective amount of diazolidinyl urea in an amount of at least about 0.01% to about 3% upon mixing with a biological sample. In some embodiments, the container comprises a non-chelating agent based anti-coagulating agent. In some embodiments, the container comprises an effective amount of acid citrate dextrose. In some embodiments, the container comprises a biological sample. In some embodiments, the diazolidinyl urea in the container is in a liquid or solid form.

The present invention also provides a container for collecting biological samples having a size from about 0.5 mL to about 50 mL and diazolidinyl urea in an amount from about 0.02 grams to about 30 grams. In some embodiments, the container includes an instruction for using the container to collect a biological sample. In some embodiments, the diazolidinyl urea is in a solid or liquid form.

DETAILED DESCRIPTION

Figure 1:
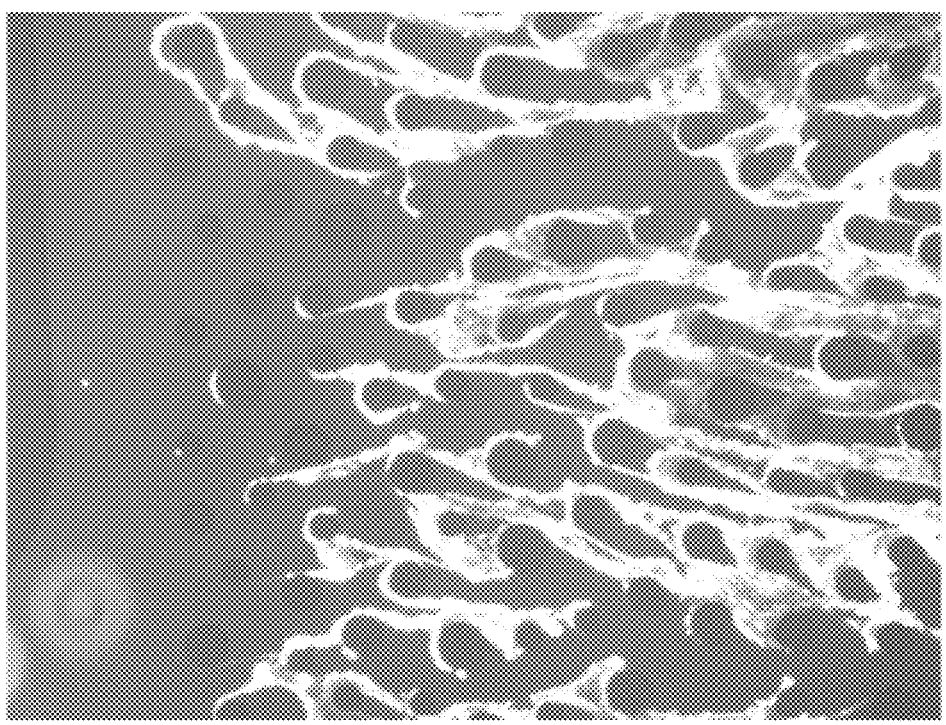
FIG. 1. Example of microfluidic device processed with blood without DU. The white strands are cell clumps.

The present invention is based at least in part on the discovery that diazolidinyl urea or its derivatives or analogs can be used to prevent or reduce cell clumping in biological samples. Accordingly the present invention provides methods and devices useful for inhibiting, preventing or reducing cell clumping in biological samples.

According to one aspect of the present invention, it provides methods for inhibiting cellular clumping in a biological sample by mixing an effective amount of diazolidinyl urea (DU) or its derivatives or analogs with the sample, e.g., where the cellular clumping is reduced at least 50% in the presence of DU compared to the absence of DU in the sample.

According to the present invention, cellular clumping includes any complex of two or more cells or cellular components, which includes without any limitation any cellular membrane encapsulated entity, e.g., microsomes, microvesicles, exosomes, mitochondria, etc. In some embodiments, cellular clumping includes two or more cells or cellular components in contact with each other, e.g., in reversible or irreversible contact with each other. In some other embodiments, cellular clumping includes two or more cells or cellular components that aggregate together in close proximity. In some other embodiments, cellular clumping includes two or more cells or cellular components in close proximity and moving as one group.

In general, cellular clumping can occur before (pre-processing or pre-testing), after or during sample processing or testing. In some instances, cellular clumping can occur in the presence or absence of sample processing. In some cases, the amount of cellular clumping increases the longer a biological sample is stored, or the more a biological sample is manipulated and/or stressed (for example by being shipped). In some cases, sample processing and pre-processing can increase cellular clumping, for example when certain reagents are added to the sample or when the biological sample is mechanically stressed. For example, mechanical stress may occur due to pipetting, passage through density gradients, centrifugation, passage through a syringe and/or passage through a device such as a microchannel or microfluidic device.

Sample processing or testing can be performed according to any standard procedure known in the art. In conjunction with the present invention, biological samples treated according to the present invention can be processed for use or testing in a variety of cellular, molecular, diagnostic and clinical assays. Exemplary assays that are contemplated for use with the present invention can include immunoassays (such as ELISA), cell sorting assays (such as but not limited to FACS), flow cytometry assays, nucleic acid assays (including RNA and DNA detection and/or isolation), protein assays (including detection and isolation), drug interaction assays, microfluidic assays, rare cell detection or quantitation, or any other variety of sorting, detection or quantitation assays that are presently used or later become available in the art. Any assay where preventing or inhibiting cellular clumping would provide a benefit is contemplated for use with methods and products of the present invention. In some embodiments, the assays are manual or automated. In some embodiments, the assays include the use of devices, such as but not limited to microfluidic devices or microchannels.

In some embodiments, cellular clumping is reduced by about 10%, about 20%, about 30%, about 40%, about 50%, about 55%, about 60%, about 65%, about 70%, about 75%, about 80%, about 85%, about 90%, about 95%, about 100%, about 150% or about 200% or more, e.g., by about 1, about 2, about 3, about 4, about 5, about 6, about 7, about 8, about 9 or about 10 fold or more, e.g., caused by the addition of diazolidinyl urea. Any suitable methods or assays known or later become available can be used to measure cellular clumping in a sample in the presence or absence of DU. For example, cellular clumping can be measured by visually surveying the extent of cellular clumping under a microscope.

According to the present invention, diazolidinyl urea includes diazolidinyl urea, and optionally its derivatives and analogs. In some embodiments, diazolidinyl urea includes any DU derivatives or analogs that are formaldehyde donors, e.g., DMDM hydantoin, imidiazolidinyl urea, or quaternium 15. In some embodiments, diazolidinyl urea includes any DU derivative or analogs that is not a preservative or stabilizing agent. In some embodiments, diazolidinyl urea includes substantially diazolidinyl urea and one or more other non-active components, e.g., components that do not materially change the activity of DU. In some embodiments, diazolidinyl urea includes a composition of diazolidinyl urea consisting essentially of DU.

In general, the effective amount of diazolidinyl urea is any amount that reduces cellular clumping in a biological sample. In some embodiments, the effective amount of DU is an amount that provides substantial anti-cellular clumping activity, but insubstantial activity for stabilizing or preserving cells or cellular components in a biological sample. In some embodiments, the effective amount of DU is an amount different from what DU is normally used for as preservatives or fixing agent, e.g., less than what DU is normally used for as preservatives or fixing agent. In some other embodiments, the effective amount of DU is an amount that achieves at least about 10%, 20%, 30%, 40% or 50% reduction in cellular clumping in a biological sample. In some embodiments, the effective amount of diazolidinyl urea is at least about 0.01% to about 3% in a biological sample. In some embodiments, the effective amount of diazolidinyl urea is at least about 0.01%, about 0.05%, about 0.1%, about 0.15%, about 0.2%, about 0.25%, about 0.5%, about 1%, about 1.5%, about 2%, about 2.5% or about 3% in a biological sample.

According to the present invention, in some embodiments diazolidinyl urea can be used in combination with one or more non-chelating agent based anti-coagulating agents. For example, DU and one or more (same or different) non-chelating agent based anti-coagulating agent can be added together or separately (sequentially or concurrently) to a biological sample. Non-chelating agent based anti-coagulating agents are those anti-coagulating agents with chelating affinity less than the chelating affinity of EDTA. Methods for determining chelating affinity are well known in the field and that are presently used or later become available in the art can be used. Any non-chelating agent based anti-coagulating agent is contemplated for use with the present invention. Examples of non-chelating agent based anti-coagulating agents can include but are not limited to acid citrate dextrose (ACD), citrate, citrate-theophylline-adenosine-dipuridamole (CTAD), citrate-pyridoxalphosphate-tris, heparin-β-hydroxy-ethyl-theophylline, polyanethol sulfonate, sodium fluoride, sodium heparin, clot activator, serum separator, thrombin and PPACK (D-phenylalanyl-L-prolyl-L-arginine chloromethyl ketone). In some embodiments, the non-chelating agent based anti-coagulating agent is acid citrate dextrose (ACD), citrate, citrate-theophylline-adenosine-dipuridamole (CTAD), citrate-pyridoxalphosphate-tris, heparin-β-hydroxy-ethyl-theophylline, polyanethol sulfonate, sodium fluoride, sodium heparin, clot activator, serum separator, thrombin or PPACK (D-phenylalanyl-L-prolyl-L-arginine chloromethyl ketone). In some embodiments, the non-chelating agent based anti-coagulating agent is acid citrate dextrose (ACD). In some embodiments, the non-chelating agent based anti-coagulating agent is citrate (citric acid).

In some embodiments, the combination of diazolidinyl urea and a non-chelating agent based anti-coagulating agent includes one or more other ingredients, e.g., preservatives, stabilizing agents, fixing agents, antibiotics, etc. In some embodiments, the combination of diazolidinyl urea and a non-chelating agent based anti-coagulating agent includes no other active ingredients, e.g., includes no other ingredients that materially change the activity of DU and non-chelating agent based anti-coagulating agent. In some embodiments, the combination of diazolidinyl urea and a non-chelating agent based anti-coagulating agent does not include a chelating based anti-coagulating agent, e.g., EDTA or other similar anti-coagulating agent. In some embodiments, the combination of DU and a non-chelating agent based anti-coagulating agent consists essentially of DU and a non-chelating agent based anti-coagulating agent, e.g., acid citrate dextrose or citrate (citric acid).

According to the present invention, a biological sample can include any unprocessed or processed cell, tissue or human secretion samples. In some embodiments, a biological sample includes any sample which contains cells or cellular components. In some embodiments, a biological sample is whole blood, blood serum, plasma, bone marrow, saliva, aqueous humour, vitreous humour, bile, breast milk, cerebrospinal fluid, cerumen (earwax), endolymph and perilymph, female ejaculate, gastric juice, mucus (including nasal drainage and phlegm), peritoneal fluid, pleural fluid, sebum (skin oil), semen, sweat, tears, vaginal excretion, vomit or urine. In some other embodiments, the biological sample is whole blood, blood serum, plasma or bone marrow.

According to the present invention, diazolidinyl urea and optionally one or more non-chelating agent based anti-coagulating agent can be added to the biological sample at the time of collection, during pre-processing or pre-testing steps or at the time of processing or testing. In some embodiments, diazolidinyl urea and optionally one or more non-chelating agent based anti-coagulating agent is added to a biological sample at the time of collection. In some embodiments, diazolidinyl urea and optionally one or more non-chelating agent based anti-coagulating agent is added to samples upon receipt or at any stage of pre-processing or pre-testing. In some embodiments, the diazolidinyl urea and optionally one or more non-chelating agent based anti-coagulating agent is mixed with the biological sample before sample processing or testing. In some embodiments, the diazolidinyl urea and optionally one or more non-chelating agent based anti-coagulating agent is mixed with the biological sample during biological sample processing or testing. In some embodiments, diazolidinyl urea and optionally one or more non-chelating agent based anti-coagulating agent is added to the samples before the samples are loaded into an assay device. In some embodiments, diazolidinyl urea and optionally one or more non-chelating agent based anti-coagulating agent is added to the samples before the samples are loaded onto a testing device, e.g., microfluidic device or microchannel.

In some embodiments, diazolidinyl urea and optionally one or more non-chelating agent based anti-coagulating agent can be included or built-in in a sample collection device, e.g., be present in the device prior to the addition of biological sample. In some embodiments, the biological samples can be collected directly into a diazolidinyl urea containing device and optionally the device may contain one or more non-chelating agent based anti-coagulating agent.

In some embodiments, biological samples are collected without addition of diazolidinyl urea. According to the present invention, when biological samples are collected without diazolidinyl, the diazolidinyl urea can be subsequently added to the biological sample. In some embodiments, diazolidinyl urea is added after biological sample collection. In some embodiments, diazolidinyl urea is added to samples during any pre-processing or pre-testing steps.

The diazolidinyl urea of the present invention can be in a solid or liquid form. In some embodiments the diazolidinyl urea is dissolved to form an about 4%, about 10%, about 20%, about 30%, about 40%, about 50%, about 60%, about 70%, about 80%, about 90% or more weight/volume (w/v) mixture. In general, diazolidinyl urea can be dissolved in any solution that would be appropriate for the intended sample processing or testing. One skilled in the art can readily determine suitable solutions for dissolving DU and optionally one or more non-chelating agent based anti-coagulating agent. In some embodiments the diazolidinyl urea is dissolved in PBS. In some embodiments the diazolidinyl urea is dissolved in PBS to form an 80% (w/v) mixture.

In some embodiments, the diazolidinyl urea is dissolved in a solution containing a non-chelating agent based anti-coagulating agent. In some embodiments, the diazolidinyl urea is dissolved in a solution containing ACD. In some embodiments, the ACD solution contains about 10 grams to about 25 grams of citrate (citric acid), about 10 grams to about 30 grams of dextrose and about 2 to about 10 grams of sodium per 1000 mL volume. In some embodiments, the ACD solution contains about 12 grams to about 25 grams of citrate (citric acid), about 13 grams to about 26 grams of dextrose and about 3 to about 6 grams of sodium per 1000 mL volume. In some embodiments, the ACD solution contains about 20 grams to about 23 grams of citrate (citric acid), about 23 grams to about 26 grams of dextrose and about 4 to about 6 grams of sodium per 1000 mL volume. In some embodiments, the ACD solution contains about 12 grams to about 14 grams of citrate (citric acid), about 13 grams to about 16 grams of dextrose and about 2 to about 4 grams of sodium per 1000 mL volume. The non-chelating agent based anti-coagulating agent solution can be made up and used according to standard methods known in the art for such solutions. Non-chelating agent based anti-coagulating agents can also be made up according to standard procedures known in the art. For example, ACD can be made up according to any standard formulation, sometimes referred to as Solution A and Solution B. ACD can be made up for example according to the formulations listed in Tables 1 and 2.

TABLE 1

ACD Formulations

| | Formulation 1* | Formulation 2* |
|---|---|---|
| citrate (citric acid $C_6H_8O_7$) | 7.3 g | 4.4 g |
| sodium citrate (dihydrate) | 22.0 g | 13.2 g |
| dextrose (monohydrate; $C_6H_{12}O_6*H_2O$) | 24.5 g | 14.7 g |

*Per 1000 mL volume.

TABLE 2

ACD Formulations

| | Formulation 3* | Formulation 4* |
|---|---|---|
| citrate (citric acid $C_6H_8O_7$) | 8.0 g | 4.8 g |
| trisodium citrate | 22.0 g | 13.2 g |
| dextrose | 24.5 g | 14.7 g |

*Per 1000 mL volume.

In some other embodiments, diazolidinyl urea is dissolved in a solution containing the non-chelating agent based anti-coagulating agent citrate (citric acid). In some embodiments, the citrate solution contains about 10 grams to about 25 grams of citrate (citric acid) per 1000 mL volume. In some embodiments, the citrate solution contains about 12 grams to about 25 grams of citrate per 1000 mL volume. In some embodiments, the citrate solution contains about 20 grams to about 23 grams of citrate (citric acid) per 1000 mL volume. In some embodiments, the citrate solution contains about 12 grams to about 14 grams of citrate (citric acid) per 1000 mL volume.

The ACD solution can be mixed with diazolidinyl urea (DU) before or after addition to the biological sample. In some embodiments, about 0.5 mL to about 5 mL of ACD/DU is added to the biological sample. In some embodiments, the ACD/DU solution is mixed at about 1 part ACD/DU to about 10 parts biological sample. In some embodiments, the ACD/DU solution is mixed at about 1 part ACD/DU to about 8 parts biological sample. In some embodiments, the ACD/DU solution is mixed at about 1 part ACD/DU to about 4 parts biological sample. In some embodiments, the ACD/DU is mixed with the biological sample at a ratio of about 1 to about 8 in an about 10 mL tube.

The citrate solution can be mixed with diazolidinyl urea (DU) before or after addition to the biological sample. In some embodiments, about 0.5 mL to about 5 mL of citrate/DU is added to the biological sample. In some embodiments, the citrate/DU solution is mixed at about 1 part citrate/DU to about 10 parts biological sample. In some embodiments, the citrate/DU solution is mixed at about 1 part citrate/DU to about 8 parts biological sample. In some embodiments, the citrate/DU solution is mixed at about 1 part citrate/DU to about 4 parts biological sample. In some embodiments, the citrate/DU is mixed with the biological sample at a ratio of about 1 to about 8 in an about 10 mL tube.

According to another aspect of the present invention, it provides sample containers with built-in DU and optionally one or more non-chelating agent based anti-coagulating agent. In some embodiments, the sample container of the present invention contains DU and one or more non-chelating agent based anti-coagulating agent, e.g., in a solid or liquid form. In some embodiments, the sample container of the present invention contains DU and acid citrate dextrose. In some embodiments, the sample container of the present invention contains DU and citrate (citric acid). In some embodiments, the diazolidinyl urea is already present in a container when the biological sample is added to the container. In some embodiments, the container includes a composition consisting essentially of diazolidinyl urea in combination with a non-chelating agent based anti-coagulating agent. In some embodiments, the container includes a composition, e.g., a liquid composition consisting essentially of diazolidinyl urea in combination with acid citrate dextrose. In some embodiments, the container includes a composition, e.g., a liquid composition consisting essentially of diazolidinyl urea in combination with citrate (citric acid). In some embodiments, the container does not contain a chelating agent based anti-coagulating agent. In some embodiments, the container does not contain EDTA. In some embodiments, the sample container of the present invention contains a liquid solution comprising or consisting essentially of DU and optionally one or more non-chelating agent based anti-coagulating agent.

In some embodiments, the sample container of the present invention has a size from about 0.1 mL to about 100 mL, from about 0.5 mL to about 50 mL, from about 1 mL to about 10 mL. In some embodiments, the sample container of the present invention has a size from about 0.5 mL to about 50 mL and contains DU at a concentration of about 4%, about 5%, about 10%, about 20%, about 30%, about 40%, about 50% or about 60% in a liquid solution in the absence of the biological sample.

In some other embodiments, the sample container of the present invention contains an effective amount of DU, in an amount of at least about 0.01%, about 0.05%, about 0.1%, about 0.5%, about 1%, about 1.5%, about 2%, about 2.5%, about 3%, about 3.5%, about 4%, about 5%, about 6% or about 10% or more upon mixing with a biological sample.

In some other embodiments, the sample container of the present invention has a size from about 0.5 mL to about 50 mL and contains diazolidinyl urea in an amount from about 0.02 grams to about 30 grams, e.g., in a liquid or solid form. In some embodiments, the sample container has a size from about 2 mL to about 40 mL and contains diazolidinyl urea in an amount from about 0.08 grams to about 24 grams. In some embodiments, the sample container has a size from about 5 mL to about 30 mL and contains diazolidinyl urea in an amount from about 0.2 grams to about 18 grams. In some embodiments, the sample container has a size from about 10 mL to about 20 mL and contains diazolidinyl urea in an amount from about 0.4 grams to about 12 grams. In some embodiments, the sample container has a size of about 10 mL and contains diazolidinyl urea in an amount from about 0.4 grams to about 6 grams.

In some embodiments, the sample container can also optionally include an instruction for using the sample container of the present invention to collect or receive a biological sample. According to the present invention, diazolidinyl urea individually or collectively with one or more non-chelating agent based anti-coagulating agent can be incubated with a biological sample for 1 minute, 5 minutes, 10 minutes, 15 minutes, 20 minutes, 25 minutes, 30 minutes, 45 minutes, 1 hour, 4 hours, 8 hours, 12 hours, 24 hours, 36 hours, 48 hours, 72 hours, 96 hours or more.

According to the present invention, the sample container of the present invention can have built-in DU and optionally one or more non-chelating agent based anti-coagulating agent either directly inside the sample container or provided in a separate container or device. Accordingly, the present invention provides a sample kit including a sample container and a reagent container, e.g., DU container. In some embodiments, the sample kit includes just the sample container containing DU and a non-chelating agent based anti-coagulating agent inside the sample container. In some embodiments, the sample kit includes the sample container containing one or more non-chelating agent based anti-coagulating agent and the reagent container containing DU. In some embodiments, the sample kit includes the sample container and the reagent container containing DU and one or more non-chelating agent based anti-coagulating agent.

In some embodiments, the reagent container is a syringe. For example, syringes containing concentrated diazolidinyl urea can be included with the sample kit. Once biological samples are collected in the sample container, diazolidinyl urea can then be subsequently added to the biological sample in the sample container. In some embodiments, the diazolidinyl urea can be injected into the sample container prior to or after addition of the biological sample. In some embodiments, the concentration of diazolidinyl urea in the syringe is from about 4% to about 60%, e.g., for a sample container in a size from about 0.5 mL to about 50 mL. In some embodiments, the concentration of diazolidinyl urea in the syringe is from about 10% to about 50%. In some embodiments, the concentration of diazolidinyl urea in the syringe is from about 15% to about 40% in the absence of the biological sample. In some embodiments, the concentration of diazolidinyl urea in the syringe is from about 20% to about 30%. In some embodiments, the concentration of diazolidinyl urea in the syringe is from about 0.1% to about 30%. In some embodiments, the concentration of diazolidinyl urea in the syringe is from about 0.08% to about 24%. For all the concentrations provided in this paragraph, the corresponding volume of the sample container is from about 0.5 mL to about 50 mL.

In some embodiments, the diazolidinyl urea of the present invention is in a solid, semi-solid or liquid form. For example, if the diazolidinyl urea is in a solid form in a sample container or a reagent container, a liquid solution could be added to the diazolidinyl urea prior to addition or exposure of diazolidinyl urea to a biological sample. Methods for diluting solids into solutions are well known in the field.

EXAMPLES

The following examples are offered to illustrate, but not to limit the claimed invention.

Example 1

Treatment of Biological Samples with Diazolidinyl Urea

Diazolidinyl urea has an empirical formula of $C_8H_{14}N_4O_7$. Its CAS number is [78491-02-08].

In this experiment, DU was dissolved in PBS to make an 80% (w/v) aqueous concentrated solution. The concentrated solution was then added to biological samples in such a way as to yield a final working concentration of 2%. Biological samples were gently mixed with DU solution to ensure equal distribution of DU, and the resulting mixture was incubated at room temperature for at least 30 minutes.

Samples were then processed according to pre-determined protocols.

FIG. 1 provides an example of samples without being treated with DU and processed through a microfluidic device. The white strands are cell clumps.

Figure 2:
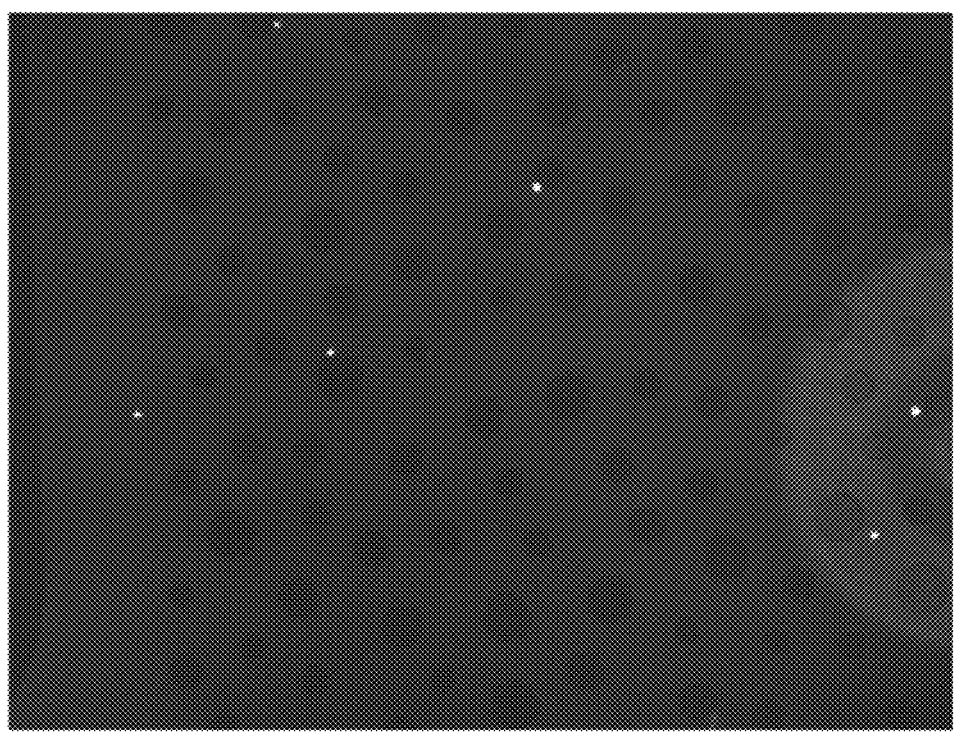
FIG. 2. Example of microfluidic device processed with blood containing DU (after incubating samples overnight with 2% DU).

FIG. 2 provides an example of samples being treated with DU and processed through a microfluidic device (for this particular experiment, the sample and DU were incubated overnight).

Figure 3:
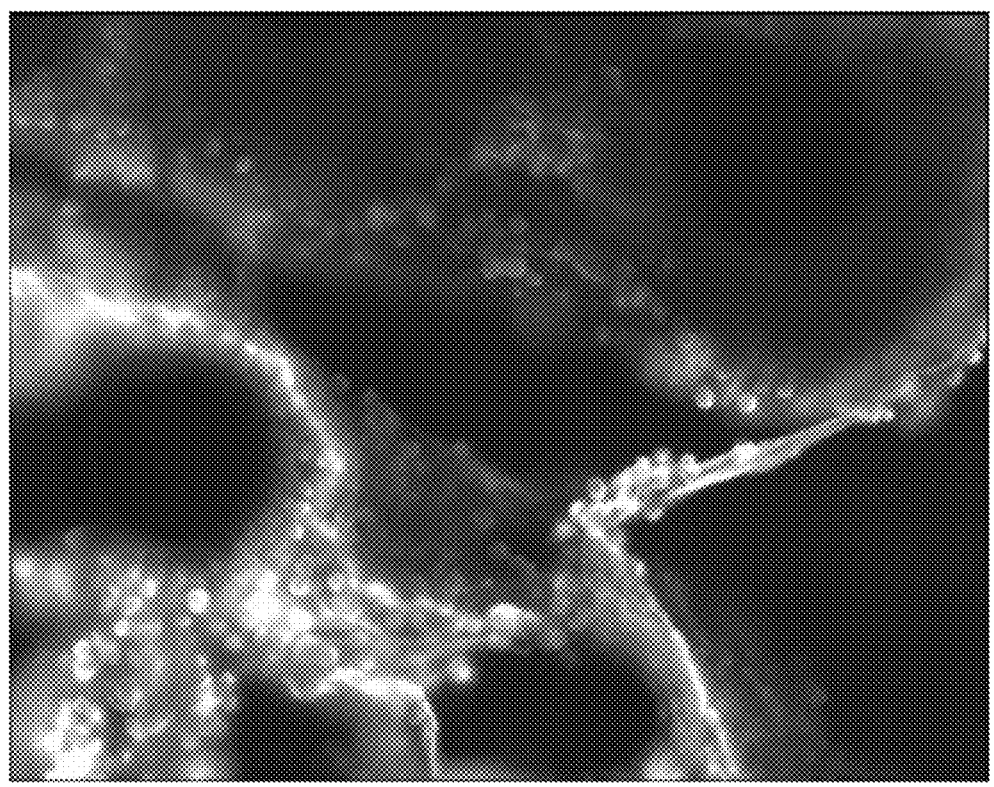
FIG. 3. Example of microfluidic device processed with blood without DU.

FIG. 3 provides another example of samples without being treated with DU and processed through a microfluidic device.

Figure 4:
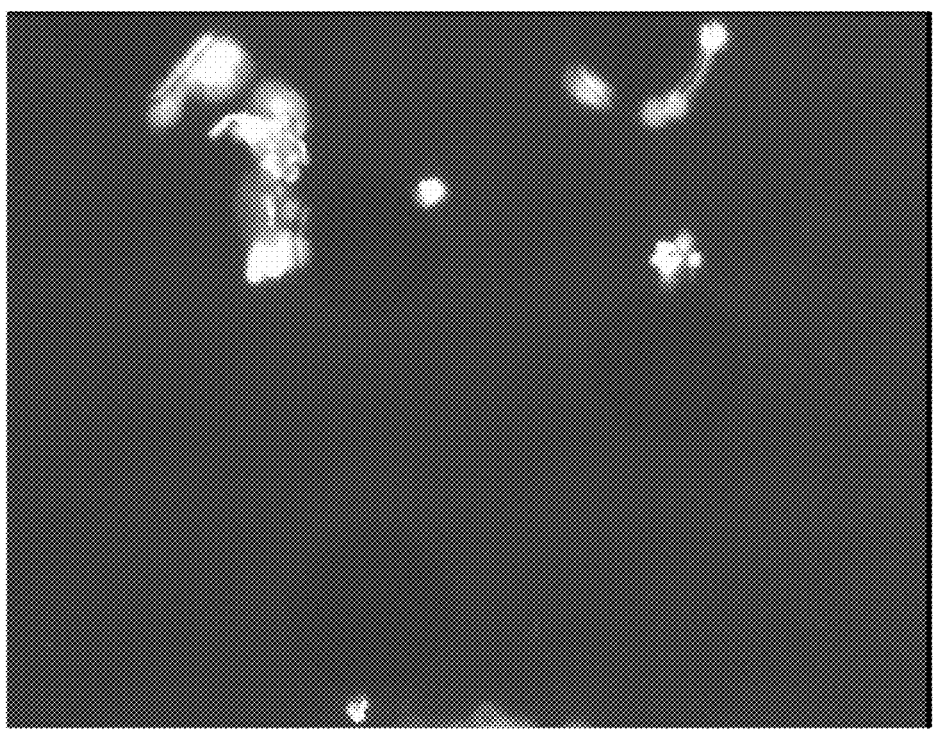
FIG. 4. Example of microfluidic device processed with blood containing DU (after incubating samples for 30 minutes with 2% DU).

FIG. 4 provides another example of samples being treated with DU and processed through a microfluidic device (for this particular experiment, the sample and DU were incubated for 30 minutes.

These experiments demonstrate that DU treatment provides great improvement for reducing cellular clumping.

All publications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

The invention claimed is:

1. A method of inhibiting cellular aggregation in a biologically active sample comprising mixing an effective amount of diazolidinyl urea with a sample of viable cells, wherein the effective amount of diazolidinyl urea is in a concentration of about 0.01% to about 3% upon mixing with the sample of viable cells.

2. The method of claim 1, further comprising mixing an effective amount of diazolidinyl urea in combination with a non-chelating agent based anti-coagulating agent with the sample.

3. The method of claim 1, further comprising mixing an effective amount of diazolidinyl urea in combination with acid citrate dextrose with the biological sample.

4. The method of claim 1, wherein the diazolidinyl urea is mixed with the sample before or during a biological sample processing or testing.

5. The method of claim 1, wherein the diazolidinyl urea is in a solid or liquid form in a container and wherein the biological sample is added to the container.

6. The method of claim 1, wherein the biological sample is selected from the group consisting of whole blood, blood serum, plasma and bone marrow.

7. The method of claim 1, wherein upon mixing with the effective amount of diazolidinyl urea the biological sample is suitable for use in a microchannel for cell capturing.

8. The method of claim 1, wherein the effective amount of diazolidinyl urea in the biological sample provides for improved cell capture in a microchannel as compared to that in the absence of diazolidinyl urea in the biological sample.

9. A method of inhibiting cellular aggregation in a biological sample comprising mixing an effective amount of diazolidinyl urea with the sample, wherein cellular aggregation is reduced in the presence of diazolidinyl urea compared to the absence of diazolidinyl urea in the sample, wherein the effective amount of diazolidinyl urea is about 0.01% to about 3% upon mixing with the biological sample, and wherein upon mixing with the effective amount of diazolidinyl urea the biological sample is suitable for use in a microchannel for cell capturing.

10. The method of claim 1, wherein the effective amount of diazolidinyl urea is about 0.1% to about 2.5% upon mixing with the biological sample.

11. The method of claim 1, wherein the effective amount of diazolidinyl urea is about 0.2% to about 2% upon mixing with the biological sample.

* * * * *